(12) United States Patent
Ferree

(10) Patent No.: US 6,419,702 B1
(45) Date of Patent: Jul. 16, 2002

(54) TREATING DEGENERATIVE DISC DISEASE THROUGH TRANSPLANTATION OF THE NUCLEUS PULPOSIS

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 23 days.

(21) Appl. No.: 09/639,309

(22) Filed: Aug. 14, 2000

Related U.S. Application Data

(60) Provisional application No. 60/148,913, filed on Aug. 13, 1999.

(51) Int. Cl.[7] .................................................. A61F 2/44
(52) U.S. Cl. ................................... 623/17.11; 424/93.7
(58) Field of Search ........................... 623/17.11–17.16, 623/11.11, 902, 908, 915; 424/93.7

(56) References Cited

U.S. PATENT DOCUMENTS

| | | | | |
|---|---|---|---|---|
| 5,514,180 A | * | 5/1996 | Heggeness et al. | 623/17.11 |
| 5,545,229 A | * | 8/1996 | Parsons et al. | 623/17.11 |
| 6,060,053 A | * | 5/2000 | Atala | 424/93.7 |
| 6,077,987 A | * | 6/2000 | Breitbart et al. | 623/11.11 |
| 6,187,048 B1 | * | 2/2001 | Milner et al. | 623/17.12 |
| 6,197,586 B1 | * | 3/2001 | Bhatnagar et al. | 435/395 |
| 6,231,615 B1 | * | 5/2001 | Preissman | 623/23.73 |
| 6,352,557 B1 | * | 3/2002 | Ferree | 623/17.11 |

OTHER PUBLICATIONS

Lumbar Intervertebral Disc Transfer a Canine Study Steven L. Frick MD et al. Spine vol. 19 No. 16, pp 1826–1835.*
Orthipedics Today, Jul. 2000. "Proceedings 13th Annual Meeting" North American Spine Society, Oct. 1998. "Proceedings 14th Annual Meeting" North American Spine Society, Oct. 1999.

* cited by examiner

Primary Examiner—David H. Willse
Assistant Examiner—Suzette J. Jackson
(74) Attorney, Agent, or Firm—Gifford, Krass, Groh, Sprinkle, Anderson & Citkowski, PC

(57) ABSTRACT

Living nucleus pulposis cells and extracellular matrix obtained from recently deceased human or animal donors are used to restore disc function and eliminate pain in patients with disc disease. In the preferred embodiment, the donor nucleus is morselized to allow insertion through a small puncture in the annulus fibrosis with a needle and syringe. Additional therapeutic substances like culture medium, growth factors, differentiation factors, hydrogels polymers, antibiotics, anti-inflammatory medications, or immunosuppressive medications could be added to the transplanted nucleus pulposis tissue.

11 Claims, No Drawings

TREATING DEGENERATIVE DISC DISEASE THROUGH TRANSPLANTATION OF THE NUCLEUS PULPOSIS

REFERENCE TO RELATED APPLICATIONS

This application claims priority of U.S. provisional patent application Ser. No. 60/148,913, filed Aug. 13, 1999, the entire contents of which are incorporated herein by reference.

FIELD OF THE INVENTION

This invention relates generally to the treatment of diseased or traumatized intervertebral discs, and more particularly, to transplantation of the nucleus pulposis in conjunction with such treatment.

BACKGROUND OF THE INVENTION

Intervertebral discs provide mobility and a cushion between the vertebrae. At the center of each disc is the nucleus pulposus which, in the adult human, is composed of cells and an insoluble extracellular matrix which is produced by the nucleus itself. The extracellular matrix is composed of collagen, proteoglycans, water, and noncoliagenous proteins. The nucleus pulposus is surrounded by the annulus fibrosis, which is composed of cells (fibrocyte-like and chondrocyte-like), collagen fibers, and non-fibrillar extracellular matrix. The components of the annulus are arranged in 15–25 lamellae around the nucleus pulposus.

The cells of the nucleus pulposus have chondrocyte-like features. In an adult human, the cells of the nucleus pulposus obtain nutrients and eliminate waste by diffusion through blood vessels in the endplates of the vertebrae adjacent to the disc. Blood vessels do not course into the nucleus pulposis. The relative vascular isolation of the nucleus pulposis imparts isolation of nucleus pulposis cells from the body's immune system.

To date, the treatment of degenerative disc disease has relied for the most part on eliminating the defective disc or disc function. This may be accomplished by fusing the vertebra on either side of the disc. In terms of replacement, most prior-art techniques use synthetic materials to replace the entire disc or a portion thereof. My pending U.S. patent application Ser. No. 09/415,382 discloses disc replacement methods and apparatus using synthetic materials.

Unfortunately, disc replacement using synthetic materials does not restore normal disc shape, physiology, or mechanical properties. Synthetic disc replacements tend to wear out, resulting in premature failure. The problems associated with the wear of prosthetic hip and knees are well known to those skilled in orthopedic surgery. The future of treating degenerative disc disease therefore lies in treatments which preserve disc function. If disc function could be restored with biologic replacement or augmentation, the risk of premature wearout would be minimized, if not eliminated.

SUMMARY OF THE INVENTION

This invention is directed to a method of treating a diseased or traumatized intervertebral disc through the transplantation of nucleus pulposis cells in conjunction with the extracellular matrix. Broadly according to the method live nucleus pulposis cells are harvested from a human or animal donor, such that the harvest includes at least a portion of the extracellular matrix, after which the harvested cells and extracellular matrix are introduced into the disc being treated. The harvested nucleus pulposis cells are preferably kept viable until placed into the disc being treated.

A preferred embodiment includes morselizing the harvested nucleus pulposus cells and extracellular matrix, forming a passageway through the annulus fibrosis, and transplanting the harvested nucleus pulposus cells and extracellular matrix into the disc through the passageway. For example, the harvested nucleus pulposus cells and extracellular matrix may be introduced into the disc using a needle and syringe or small cannula.

One or more therapeutic substances may be added to the harvested nucleus pulposus cells and extracellular matrix including culture media, growth factors, differentiation factors, hydrogels, polymers, antibiotics, anti-inflammatory medications, or immunosuppressive medications. Alternatively the step of transplanting the harvested nucleus pulposus cells and extracellular matrix may include percutaneously or laparoscopically injecting the engineered disc tissue into the disc being treated.

DETAILED DESCRIPTION OF THE INVENTION

As discussed above, the relative vascular isolation of the nucleus pulposis imparts isolation of nucleus pulposis cells from the body's immune system. This invention exploits the lack of an immune system response to the transplantation of nucleus pulposis cells and extracellular matrix harvested from another human or animal.

According to the method, the nucleus pulposis is preferably harvested from a live human, though recently deceased human or animal donors may alternatively be used. Depending upon the extent of the harvest, the recipient may function at least in part as a donor, or the tissues from others, including fetal sources, may be used, preferably having a familial relationship to minimize or avoid the need for immunosuppressive substances. Guidelines for tissue procurement including surgical technique of removal, number of hours between death of the donor and tissue procurement, and testing of the donor for infectious disease, are well described in the literature.

Similarly, the guidelines for storage of living tissues are well known to those skilled in the art. The text "Organ Preservation for Transplantation" by Karow and Pego, 1981, describes such methods. Briefly, the tissue storage method must maintain cell viability and preserve sterility. Examples of present storage methods include: refrigeration, refrigeration with tissue culture medium such as: hemolyzed serum, autologous serum, Medium 199 with 5% dextran (McCarey-Kaufinan medium), Medium 199 with chondroitin sulfate, Medium 199 supplemented with inorganic salts, short chain fatty acids, and/or ketone bodies, and cryopreservation techniques, among others. Details are provided in U. S. Pat. Nos. 4,695,536 and 4,873,186, the entire contents of which are incorporated herein by reference.

To minimize exposure to the recipient's immune system, the harvested nucleus pulposis is preferably inserted through a small hole in the annulus fibrosis using a blunt-tipped needle or cannula forced through the laminae. Upon withdraw of the needle, after injecting the transplanted nucleus pulposis, the separated fibers of the lamella return to their normal position, thereby sealing the annulus.

The annulus fibrosis is thicker in the anterior and lateral portion of the disc. Thus, in the preferred embodiment, the needle would be inserted into the anterior or lateral portion of the disc. Those skilled in the art will realize the needle could be directed into the lateral portion of the disc percutaneously with fluourscopic guidance and into the anterior portion of the disc laparoscopically.

The host nucleus pulposis may be morselized to allow insertion into the disc through a small cannula or needle. The increased surface area of the nucleus pulposis after morsellization may also aid diffusion of nutrients and wastes products to and from transplanted disc cells. Alternatively large sections of the transplanted nucleus pulposis could be added to the disc if the annular defect was sealed after transplantation.

The transplanted nucleus is preferably added to the patient's nucleus pulposis. Alternatively, the patient's nucleus could be removed with standard techniques (enzymatically (chymopapain) or with the aid of a laser, suction device, shaver, or other surgical instrument). If the nucleus is removed the hole in the annulus should be small and sealed to prevent the ingrowth of vascular tissue. Vascular ingrowth could lead to a graft versus host reaction.

Additional therapeutic substances could be added to the transplanted nucleus. For example, resorbable culture medium, tissue growth or differentiation factors (recombinant generated morphogenetic proteins, PDGF, TGF-$\beta$, EGF/TGF-$\alpha$, IGF-1, $\beta$PFGF), hydrogels, absorbable or nonresorbable synthetic or natural polymers (collagen, fibrin, polyglycolic acid, polylactic acid, polytetrafluoroethylene, etc.), antibiotics, anti-inflammatory medication, immunosuppressive medications, etc. could be beneficial.

I claim:

1. A method of treating a diseased or traumatized intervertebral disc having a nucleus and annulus fibrosis, comprising the steps of:

harvesting live, nucleus pulposus cells from a human or animal donor, the harvest including at least a portion of the etacellular matrix; and transplanting the harvested cells and extracellular matrix into the disc being treated through a passageway in the annulus fibrosis.

2. The method of claim 1, further including the step of:

morselizing the harvested nucleus pulposus cells and extracellular matrix prior to tarnsplanting.

3. The method of claim 1, further including the step of adding one or more therapeutic substances to the harvested nucleus pulposus cells and extracellular matrix.

4. The method of claim 3, wherein the therapeutic substances include one or more of the following:

culture media, growth factors, differentiation factors, hydrogels, polymers, antibiotics, anti-inflammatory medications, or immunosuppressive medications.

5. The method of claim 1, wherein the step of transplanting the harvested nucleus pulposus cells and extracellular matrix into the disc includes injecting the engineered disc tissue into the disc through a needle and syringe or small cannula.

6. The method of claim 1, wherein the step of transplanting the harvested nucleus pulposus cells and extracellular matrix includes percutaneously or laparoscopically injecting the engineered disc tissue into the disc being treated.

7. The method of claim 1, further including the step of keeping the harvested harvested nucleus pulposus cells viable until placed into the disc being treated.

8. A method of preparing a product to treat a diseased or traumatized intervertebral disc having a nucleus and annulus fibrosis, comprising the steps of:

harvesting live, nucleus pulposus cells from a human or animal donor, the harvest including at least a portion of the extracellular matrix;

morselizing the harvested nucleus pulposus cells and extracellular matrix to permit introduction of the product through a passageway formed in the annulus fibrosis; and keeping the product viable until use.

9. A product produced according to the method of claim 8.

10. The product of claim 9, further including one or more therapeutic substances.

11. The product of claim 10, wherein the therapeutic substances include one or more of the following:

culture media, growth factors, differentiation factors, hydrogels, polymers, antibiotics, anti-inflammatory medications, or immunosuppressive medications.

* * * * *

UNITED STATES PATENT AND TRADEMARK OFFICE
CERTIFICATE OF CORRECTION

PATENT NO.    : 6,419,702 B1
DATED         : July 16, 2002
INVENTOR(S)   : Bret A. Ferree It is certified that error appears in the above-identified patent and that said Letters Patent is hereby corrected as shown below:

Column 1,
Line 23, replace "noncoliagenous" with -- noncollagenous --.

Column 2,
Line 48, replace "Kaufinan" with -- Kaufman --.

Column 3,
Line 34, replace "etacellular" with -- extracellular --.
Line 34, replace "tarsnplanting" with -- transplanting --.

Column 4,
Line 18, delete one "harvested".

Signed and Sealed this

First Day of April, 2003

JAMES E. ROGAN
*Director of the United States Patent and Trademark Office*